(12) United States Patent
Bain et al.

(10) Patent No.: US 8,222,278 B2
(45) Date of Patent: Jul. 17, 2012

(54) TREATMENT OF ATTENTION-DEFICIT/HYPERACTIVITY DISORDER

(75) Inventors: Earle E. Bain, Libertyville, IL (US); Walid M. Abi-Saab, Dornach (CH); Sandeep Dutta, Gurnee, IL (US); Tushar S. Garimella, Skokie, IL (US); Walid M. Awni, Libertyville, IL (US); Mario D. Saltarelli, Lake Bluff, IL (US)

(73) Assignee: Abbott Laboratories, Abbott Park, IL (US)

( * ) Notice: Subject to any disclaimer, the term of this patent is extended or adjusted under 35 U.S.C. 154(b) by 162 days.

(21) Appl. No.: 12/475,440

(22) Filed: May 29, 2009

(65) Prior Publication Data
US 2010/0144795 A1    Jun. 10, 2010

Related U.S. Application Data

(60) Provisional application No. 61/058,467, filed on Jun. 3, 2008.

(51) Int. Cl.
*A61K 31/44* (2006.01)
(52) U.S. Cl. .................................................. 514/338

(58) Field of Classification Search ................ 514/339, 514/338
See application file for complete search history.

(56) References Cited

U.S. PATENT DOCUMENTS

| | | | |
|---|---|---|---|
| 6,809,105 B2 | 10/2004 | Schrimpf et al. | |
| 7,351,833 B2 | 4/2008 | Wayne et al. | |
| 7,354,937 B2 | 4/2008 | Buckley et al. | |
| 7,498,444 B2 | 3/2009 | Wayne et al. | |
| 7,538,226 B2 | 5/2009 | Buckley et al. | |
| 2004/0242641 A1* | 12/2004 | Buckley et al. | 514/337 |
| 2004/0242644 A1 | 12/2004 | Buckley et al. | |

FOREIGN PATENT DOCUMENTS
WO   WO2004/106342   12/2004

OTHER PUBLICATIONS
International Search Report dated Sep. 24, 2009.

* cited by examiner

*Primary Examiner* — Jennifer M Kim
(74) *Attorney, Agent, or Firm* — Lisa V. Mueller; Michael Best & Friedrich LLP

(57) ABSTRACT

3-(5,6-Dichloro-pyridin-3-yl)-1S,5S-3,6-diazabicyclo[3.2.0]heptane and salts thereof are effective nicotinic receptor agonist compounds that demonstrated pharmacological effect for symptoms associated with attention-deficit/hyperactivity disorder.

3 Claims, 2 Drawing Sheets

Disposition of Study Subjects

Two Doses in Separate Cohorts Demonstrated Statistically Significant Differences from Placebo for Primary Endpoint (CAARS-Inv Total Score)

* one-tailed *P* value defined *a priori*; statistically significant at *P*<.05 level compared with placebo

TREATMENT OF ATTENTION-DEFICIT/HYPERACTIVITY DISORDER

CROSS-REFERENCE TO RELATED APPLICATIONS

This patent application claims priority to U.S. Provisional Patent Application No. 61/058,467, filed on Jun. 3, 2008, the entirety of which is incorporated herein by reference.

BACKGROUND OF THE INVENTION

1. Technical Field

The invention relates to a method of treating psychiatric disorders and, in particular, symptoms associated with attention-deficit/hyperactivity disorder. The method involves administering a neuronal nicotinic acetylcholine receptor ligand. such as 3-(5,6-dichloro-pyridin-3-yl)-1S,5S-3,6-diazabicyclo[3.2.0]heptane, a neuronal nicotinic acetylcholine receptor agonist, for treatment of attention-deficit/hyperactivity disorder.

2. Description of the Related Technology

For over a decade, researchers have investigated the pharmacological effects of compounds affecting neurotransmitter release in neuronal nicotinic acetylcholine receptors (nAChRs). Such research has reported on the potential effects of neuronal nicotinic acetylcholine receptor ligands in a variety of disease states, including various cognitive disorders, for example conditions such as attention-deficit/hyperactivity disorder (ADHD), Alzheimer's disease, and other disorders and addictions, for example nicotine addiction. The neuronal nicotinic acetylcholine receptor ligand, varenicline, currently is available for commercial use for treatment of smoking cessation.

However, nAChR ligands compounds that affect nAChR receptors in a beneficial manner can also produce undesireable effects in subjects and patients. Adverse effects such as nausea, vomiting. and emesis have been associated with nAChR ligands use, and particularly associated with nicotinic acetylcholine receptor subtype α3. While the beneficial pharmacological effects of nAChR ligands are desireable, the experience of adverse effects can limit pharmacological use. In particular, ADHD is associated with functional impairments such as poor academic or occupational performance, problems in peer relationships, injuries, traffic violations and accidents as well as psychiatric comorbidities including mood, anxiety and substance use disorders. Approximately 30% of patients discontinue stimulant medications due to an inadequate response or intolerable side effects. Sixty-five to 85% of children will continue to meet criteria or exhibit partial symptoms of ADHD into adulthood. Cognitive dysfunction, including impairments in attention and executive function, is common in adolescents and adults with ADHD and increases their risk for academic and occupational difficulties.

It would be beneficial to provide a nicotinic acetylcholine receptor ligand for treatment of nAChR-mediated conditions, for example disorders such as ADHD, Alzheimer's disease, schizophrenia or other conditions related to cognitive function, and addictions, such as addiction to nicotine or treatment of smoking cessation. There remains a need for providing a nicotinic acetylcholine receptor ligand that treats such conditions in a safe and efficacious manner. Such method of treatment could provide significant advantage over current therapies, particularly for treatment of attention-deficit hyperactivity disorder, where treatment can involve the administration of controlled substances, which can be subject to abuse.

SUMMARY OF THE INVENTION

It has been found that 3-(5,6-dichloro-pyridin-3-yl)-1S, 5S-3,6-diazabicyclo[3.2.0]heptane and salts thereof are effective compounds for treatment of symptoms associated with attention-deficit/hyperactivity disorder. Moreover, administration of 3-(5,6-dichloro-pyridin-3-yl)-1S,5S-3,6-diazabicyclo[3.2.0]heptane to human patients reduced the severity of symptoms associated with attention-deficit/hyperactivity disorder in patients in a generally well tolerated manner. 3-(5,6-Dichloro-pyridin-3-yl)-1S,5S-3,6-diazabicyclo [3.2.0]heptane (ABT-894) demonstrated statistically significant efficacy compared to placebo in the treatment of the core symptoms of ADHD in human patients.

DETAILED DESCRIPTION OF THE INVENTION

Figure 1:
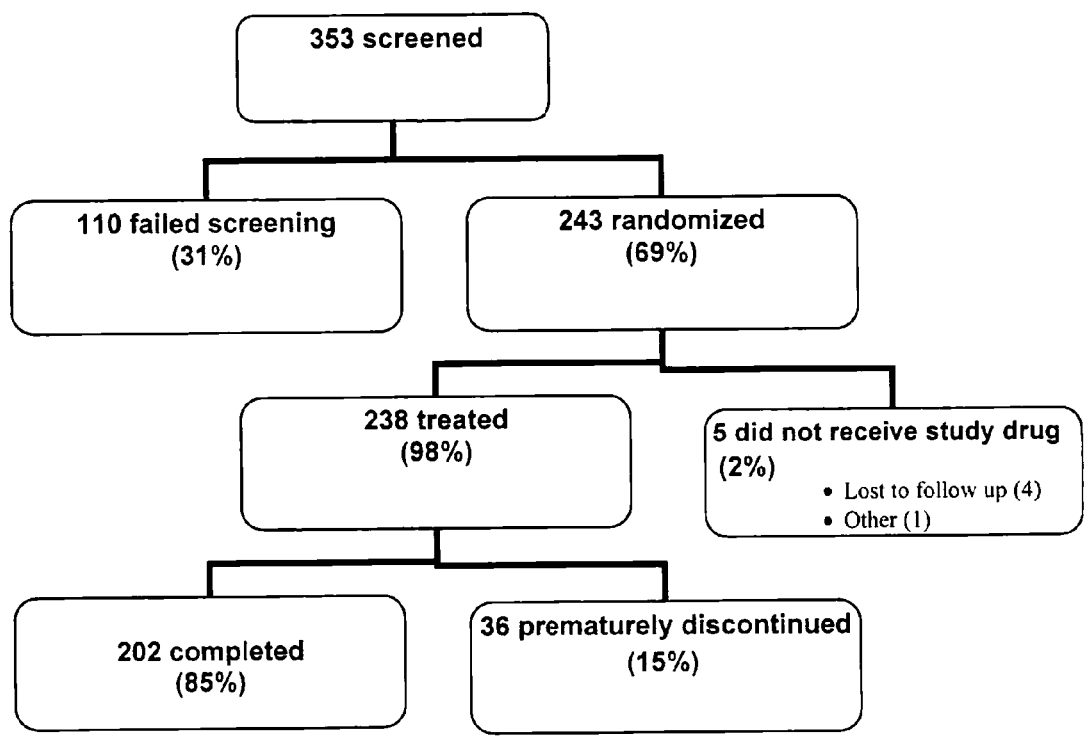
FIG. 1 graphically depicts the disposition of the study subjects of the ABT-894 Adult ADHD Dose-Ranging Study.

The present invention relates to a method of treating attention-deficit/hyperactivity disorder in humans, and particularly for the treatment of attention-deficit/hyperactivity disorder. In one embodiment, the methods comprise administering to a patient in need of such treatment an effective amount of an active agent, 3-(5,6-dichloro-pyridin-3-yl)-1S,5S-3,6-diazabicyclo[3.2.0]heptane.

The 3-(5,6-dichloro-pyridin-3-yl)-1S,5S-3,6-diazabicyclo [3.2.0]heptane active agent has been previously described in U.S. Pat. No. 6,809,105, issued Oct. 26, 2004. While the use of 3-(5,6-dichloro-pyridin-3-yl)-1S,5S-3,6-diazabicyclo [3.2.0]heptane is preferred, other compounds disclosed in U.S. Pat. No. 6,809,105 can be used. Preparation and use of 3-(5,6-dichloro-pyridin-3-yl)-1S,5S-3,6-diazabicyclo[3.2.0] heptane active is described in U.S. Pat. No. 7,354,937, issued Apr. 8, 2008: U.S. Pat. No. 7,538,226, issued May 26, 2009: U.S. Pat. No. 7,351,833, issued Apr. 1, 2008: and U.S. Pat. No. 7,498,444, issued Mar. 3, 2009, and their related applications. Such patents and their related applications are herein incorporated by reference.

A preferred salt for administering in the attention-deficit/hyperactivity disorder therapy herein is the 3-(5,6-dichloro-pyridin-3-yl)-1S,5S-3,6-diazabicyclo[3.2.0]heptane benzenesulfonate (or besylate) salt.

The amount of the active agent administered can vary with the patient, the route of administration, and the result sought. Optimum dosing regimens for particular patients can be determined by one skilled in the art using the guidance and dosing information provided herein.

In accordance with the present invention, the active agent can be administered in any convenient manner. Examples of suitable methods for administration include, but are not limited, orally, sublingually. rectally, parentally. (including subcutaneously intrathechally, intramuscularly, and intravenously), or transdermally. The most preferred route of administration is the oral route.

The active agents of the invention can be administered in the form of a pharmaceutical composition or compositions that contain one or both active agents in an admixture with a pharmaceutical carrier. The pharmaceutical composition can be in dosage unit form such as tablet, capsule, sprinkle capsule, granule, powder, syrup, suppository, injection, or the like.

An effective treatment for attention-deficit/hyperactivity disorder described herein provides an effective means for improving the cognitive attention or other efficacy outcomes of a patient while minimizing the adverse side effects that can be associated with such medications. Examples of such side effects can include, for example, nausea, fatigue, headache, sleep disturbances, and the like.

Certain aspects of the invention are described in greater detail in the non-limiting Examples that follow:

Example 1

Experimental Details

Subjects

A clinical study (Study A) was conducted to assess the safety and efficacy of ABT-894 compared to placebo in adults with ADHD and to evaluate the dose-response relationship.

A total of 243 subjects aged 18 to 60 years old meeting DSM-IV-TR criteria for ADHD were randomized across the 5 dose groups. Male or female patients were included. Patients were excluded if they had an Axis I psychiatric disorder, for example major depression, generalized anxiety disorder (GAD), or any lifetime history of schizophrenia, schizoaffective disorder, bipolar disorder, obsessive-compulsive disorder (OCD), or mental retardation; had taken atomoxetine within three months prior to screening, or was taking psychotropic medication, including nicotine replacement therapy or varenicline. The disposition of the study subjects is further discussed with the study results below.

Study Design

Subjects in each dose group received, in random order, both ABT-894 and placebo according to a 2×2 crossover design. Each treatment period was 4 weeks separated by a 2-week washout period. The crossover study design and dosing schedule are shown in Table 1.

Randomization, Medication Dosing, and Dispensing

Each site was assigned to one of two cohorts (Cohort A or Cohort B) in approximately a 3:2 ratio. Subjects in Cohort A were randomized in equal proportions to one of 6 treatment sequences in 3 dose groups, and subjects in Cohort B were randomized in equal proportions to one of 4 treatment sequences in 2 dose groups, as shown in Table 1. Within each dose group subjects received either ABT-894 or atomoxetine in Period 1 and placebo in Period 2, or placebo in Period 1 and ABT-894 or atomoxetine in Period 2.

The study medication was dispensed in the form of a capsule. Each capsule contained ABT-894, atomoxetine, or placebo. The capsules were made to look identical.

Visits and Measurements

Subjects were seen for four weeks with a two week washout period and then seen for an additional four weeks. During each visit, blood pressure, heart rate, weight, medication accountability and tolerability, and adverse effects were assessed. Reportable adverse effects were new symptoms or illnesses that emerged during treatment or those that had an increase in severity compared with baseline.

Endpoints and Measures of Outcome

The primary efficacy endpoint was the Conners' Adult ADHD Rating Scale—Investigator Rated (CAARS:Inv) Total Score (18 items) at the final evaluation of each 4-week treatment period. The CAARS:Inv was assessed at baseline and Days 7. 14. 21, and 28 of each period. Each CAARS:Inv item was rated on a 4-point scale of frequency of occurrence (0=not at all, never; 3=very much. very frequently) during the previous 7 days.

Secondary efficacy endpoints included the CAARS:Inv Inattentive and Hyperactive/Impulsive Subscale Scores, Clinical Global Impression-ADHD-Severity Scale (CGI-ADHD-S). Adult ADHD Investigator Symptom Report Scale (AISRS), including total and subscales, and the Self-rated Connors Adult ADHD Rating Scale (CAARS-Self). Health outcomes including the Adult ADHD Quality of Life Scale (AAQoL) and Work Productivity and Activity Impairment Questionnaire (WPAI) were used to evaluate the validity of these scales in this study population for use in subsequent clinical trials.

Statistical Analysis

The primary analysis was performed on each dose group separately according to the Statistical Analysis Plan (SAP). The primary statistical model that was used for analyzing the primary efficacy variable, the CAARS:INV total score, and all other secondary efficacy variables was determined by a SAP specified testing procedure. The comparability between two sequences for a given dose group with respect to the difference between period-specific baselines was tested using a one-way ANCOVA with the term of treatment and the Period I baseline as the covariate at the significance level of 0.10. The equal residual effect from Period I to Period II between two different sequences for a given dose group was tested using a standard model for cross-over data analysis,

TABLE 1

Crossover study design and dosing schedule

| Cohort | Dose Group | n* | Period 1 (4 weeks) | | Period 2 (4 weeks) |
|---|---|---|---|---|---|
| A | 1 | 24 Screening | 1 mg ABT-894 QD | Washout | Placebo |
|   |   | 22 (up to 4 | Placebo | (2 weeks) | 1 mg ABT-894 QD |
| A | 2 | 20 weeks) | 2 mg ABT-894 QD | | Placebo |
|   |   | 25 | Placebo | | 2 mg ABT-894 QD |
| A | 3 | 23 | 4 mg ABT-894 QD | | Placebo |
|   |   | 24 | Placebo | | 4 mg ABT-894 QD |
| B | 4 | 28 | 4 mg ABT-894 BID | | Placebo |
|   |   | 24 | Placebo | | 4 mg ABT-894 BID |
| B | 5 | 29 | 40 mg atomoxetine BID | | Placebo |
|   |   | 24 | Placebo | | 40 mg atomoxetine BID |

*number of subjects randomized

Grizzle model, on the term of "sequence" at the significance level of 0.10.

After the study blind was broken, across 5 dose groups. all the tests accepted the null hypothesis that there was no statistically significant treatment effect for the differences between the period-specific baselines. The tests also accepted the null hypothesis that there was no period residual effect in any of the dose groups. Accordingly, the Grizzle model was used as the primary analysis model to analyze treatment group difference for CAARS:INV total score at Day 28 for each dose group. The Grizzle Model was carried out by SAS PROC Mixed with the terms of study center. sequence, subjects within sequence, period, treatment, as well as period-specific baselines as covariates.

The primary efficacy dataset included all subjects who completed both periods of the study (completers dataset).

The safety dataset consisted of all subjects who took at least one dose of study drug. The reasons for discontinuation and the treatment-emergent adverse events were summarized by the treatment under which the discontinuation or event was reported.

The treatment group differences in vital signs were analyzed using a Grizzle Model similar to the model used for the efficacy analyses with the exclusion of period-specific baselines.

Results

Subject Characteristics and Disposition

Of the 353 subjects screened, 243 were included in the randomized study. Of the patients included. 238 were treated, 5 patients did not receive study drug due to reasons not related to treatment. The study was completed by 202 of the 238 patients treated. Baseline characteristics of the patients are shown in Table 2.

TABLE 2

Subject baseline demographics (safety dataset)

| Characteristic | Overall N = 238 |
|---|---|
| Age (years), mean (SD) | 36.2 (11.85) |
| Gender, n (%) | |
| Female | 112 (47) |
| Male | 126 (53) |

TABLE 2-continued

Subject baseline demographics (safety dataset)

| Characteristic | Overall N = 238 |
|---|---|
| Race, n (%) | |
| White | 207 (87) |
| Black | 23 (10) |
| Other | 8 (3) |
| History of psychiatric disorders, n (%) | |
| Major depression | 51 (21) |
| Anxiety disorder | 7 (3) |
| Conduct disorder | 2 (<1) |
| Age at first diagnosis (years), mean (SD) | 29.6 (15.97) |
| Subjects who received past pharmacologic treatment for symptoms of ADHD, n (%) | |
| Stimulants | 117 (49) |
| Atomoxetine | 28 (12) |
| Antidepressants | 20 (8) |
| Other | 19 (8) |
| ADHD DSM-IV diagnosis subtype, n (%) | |
| Inattentive | 60 (25) |
| Hyperactive/Impulsive | 1 (<1) |
| Combined | 177 (74) |
| Tobacco Use, n (%) | |
| Non-tobacco user | 194 (82) |
| Current tobacco user | 44 (18) |

Efficacy

Figure 2:
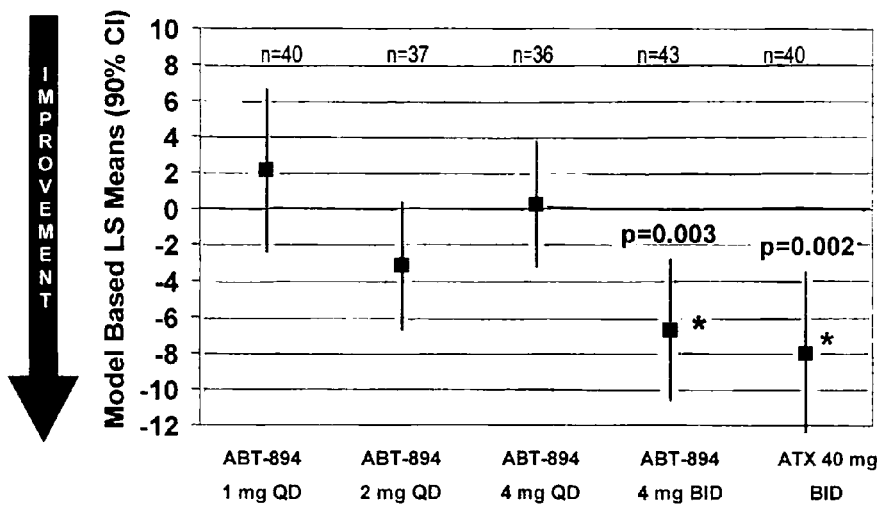
FIG. 2 graphically depicts the ABT-894 mean difference from placebo at 4 mg BID on the primary endpoint, CAARS-Inv Total Score, compared with the atomoxetine mean difference from placebo at 40 mg BID.

Administration of ABT-894 at a dose of 4 mg BID for 28 days resulted in statistically significant improvements compared with placebo in the primary efficacy measure. The results obtained were compared with atomoxetine, which is commercially available for treatment of attention-deficit/hyperactivity disorder. ABT-894 administered at a dose of 4 mg BID and atomoxetine were comparable across efficacy measures. Mean difference of ABT-894 from placebo at 4 mg BID on the primary endpoint, CAARS-Inv Total Score, and the mean difference of atomoxetine from placebo at 40 mg BID are shown in FIG. 2. Results from the CAARS Inattentive and Hyperactive/Impulsive Total Scores and Subscale Scores are presented in Table 3.

TABLE 3

ABT-894 mean difference from placebo on CAARS: Inv total scores and subscale scores at day 28 of periods 1 and 2 by dose group (completers dataset)[a]

| CAARS: Invs Total and Subscale Score | Dose of ABT-894 | | | | Atomoxetine |
|---|---|---|---|---|---|
| | 1 mg QD N = 40 | 2 mg QD N = 37 | 4 mg QD N = 36 | 4 mg BID N = 43 | 40 mg BID N = 40 |
| Total Score | 2.11 (−2.4, 6.6) N/A | −3.18 (6.7, 0.3) 0.065 | 0.23 (−3.2, 3.7) N/A | −6.69 (−10.6, −2.8) 0.003* | −7.98 (−12.5. −3.5) 0.002* |
| Inattentive | 0.94 (−1.5, 3.4) N/A | −1.92 (−3.8, −0.1) 0.043 | 0.60 (−1.5, 2.7) N/A | −4.08 (−6.4, −1.7) 0.003* | −3.89 (−6.3. −1.5) 0.004* |
| Hyperactive/ Impulsive | 0.93 (−0.2, 2.0) N/A | −0.55 (−1.4, 0.3) 0.14 | −1.07 (−2.1, −0.0) 0.048* | −1.90 (−3.0, −0.8) 0.003* | −1.43 (−2.4, −0.4) 0.01* |
| ADHD Index | 1.84 (−0.0. 3.7) N/A | −1.52 (−3.3, 0.2) 0.077 | −0.12 (−1.8, 1.5) 0.45 | −3.37 (−5.3. −1.4) 0.003* | −3.00 (−4.9, −1.1) 0.005* |

*one-sided $P < 0.05$ vs. placebo

[a]Least square means and treatment P value from ANCOVA; Total Score obtained at the end of each treatment period with baseline score within each period as a covariate.

Secondary efficacy endpoints included the CAARS:Inv Inattentive and Hyperactive/Impulsive Subscale Scores. Adult ADHD Investigator Symptom Report Scale (AISRS), an 18-item scale that uses adult-specific ADHD prompts to assess each DSM-IV-TR symptom criterion based on severity (0=not present to 3=severe) during the previous 7 days also was assessed. Subject self-rated Conners' Adult ADHD Rating Scale (CAARS:Self), which is similar to CAARS:Inv, in which each item is rated by the subject on a 4-point scale of frequency of occurrence (0=not at all, never to 3=very much, very frequently) during the previous 7 days also was assessed.

Another secondary efficacy endpoint was the Investigator-rated Clinical Global Impression-ADHD Severity Scale (CGI-ADHD-S), which is a 7-point rating scale (1=normal, not ill at all, to 7=among the most extremely ill patients) used to assess the global severity of illness due to ADHD symptoms.

Results from the CGI-ADHD-S, AISRS, and CAARS:Self are shown below in Table 4. The data support that ABT-894 dosed at 4 mg BID and atomoxetine are comparable across efficacy measures.

TABLE 4

ABT-894 mean difference from placebo on secondary outcomes measures at day 28 of periods 1 and 2 by dose group (completers dataset)[a]

| | | Dose of ABT-894 | | | | |
|---|---|---|---|---|---|---|
| | | 1 mg QD N = 40 | 2 mg QD N = 37 | 4 mg QD N = 36 | 4 mg BID N = 43 | Atomoxetine 40 mg BID |
| CGI-ADHD-S | | 0.04 (−0.3, 0.4) N/A | −0.31 (−0.6, 0.0) 0.051 | −0.06 (−0.3, 0.2) 0.353 | −0.58 (−1.0, −0.2) 0.008* | −0.45 (−0.8, −0.1) 0.021* |
| AISRS | Total Score | 3.19 (−1.2, 7.6) N/A | −2.72 (−6.4, 1.0) 0.11 | −0.13 (−3.6, 3.4) 0.476 | −8.07 (−12.2, −3.9) 0.001* | −7.18 (−11.5, −2.9) 0.004* |
| | Inattention Score | 1.72 (−0.6, 4.1) N/A | −1.59 (−3.6, 0.4) 0.096 | 0.81 (−1.2, 2.8) N/A | −4.26 (−6.6, −1.9) 0.002* | −3.81 (−6.1, −1.6) 0.003* |
| | Hyperactivity Score | 1.53 (−0.8, 3.8) N/A | −1.11 (−3.0, 0.7) 0.157 | −0.81 (−2.6, 1.0) 0.226 | −3.58 (−5.6, −1.6) 0.002* | −3.29 (−5.4, −1.2) 0.005* |
| CAARS: Self | Total Score | 3.57 (−0.4, 7.5) N/A | −2.64 (−6.6, 1.3) 0.131 | −1.13 (−5.2, 2.9) 0.321 | −7.34 (−11.6, −3.1) 0.003* | −7.12 (−10.9, −3.3) 0.002* |
| | Inattention/Memory Score | 0.60 (−0.5, 1.7) N/A | −0.23 (−1.2, 0.8) 0.349 | 0.11 (−0.9, 1.2) N/A | −1.40 (−2.5, −0.3) 0.021* | −1.56 (−2.5, −0.6) 0.004* |
| | Hyperactivity Score | 0.68 (−0.4, 1.8) N/A | −0.57 (−1.4, 0.3) 0.133 | −0.78 (−1.8, 0.2) 0.099 | −1.74 (−2.9, −0.6) 0.006* | −1.43 (−2.4, −0.5) 0.008* |
| | Impulsivity Score | 0.65 (−0.1, 1.4) N/A | −0.48 (−1.3, 0.3) 0.164 | −0.02 (−0.9, 0.9) 0.484 | −0.70 (−1.4, −0.0) 0.040* | −1.17 (−1.9, −0.5) 0.005* |
| | Problem with Self-concept Score | 0.51 (−0.2, 1.2) N/A | −0.57 (−1.6, 0.5) 0.184 | 0.33 (−0.7, 1.4) N/A | −1.39 (−2.5, −0.3) 0.018* | −0.70 (−1.5, 0.1) 0.064 |
| | ADHD Index | 2.04 (0.2, 3.9) N/A | −1.50 (−3.3, 0.3) 0.083 | −0.19 (−1.9, 1.5) 0.427 | −3.31 (−5.2, −1.4) 0.003* | −3.08 (−4.8, −1.3) 0.003* |

Improvements in the AAQol and WPAI scales correlated with changes in the primary efficacy endpoint. Treatment with ABT-894 at a dose of 4 mg BID showed a trend toward improved quality of life relative to placebo. Treatment with ABT-894 at a dose of 4 mg BID also significantly improved absenteeism. Patient-reported health outcomes measures of ABT-894 and atomoxetine (ATX) are summarized in Table 5 below.

TABLE 5

Patient-reported health outcomes analyses

| | ABT-894 4 mg BID | | | ATX 40 mg BID | | |
|---|---|---|---|---|---|---|
| | N | Mean Diff. | p-value | N | Mean Diff. | p-value |
| AAQoL Total | 42 | 6.6 | 0.053 | 40 | 7.23 | 0.032 |
| WPAI | | | | | | |
| Overall Activity Impairment (all) | 43 | −0.108 | 0.012 | 36 | −0.13 | 0.003 |
| Overall Work Impairment (employed) | 22 | −0.093 | 0.175 | 18 | −0.12 | 0.089 |
| Absenteeism (employed) | 22 | −0.007 | 0.860 | 18 | 0.019 | 0.785 |
| Impaired Work Effectiveness (employed) | 22 | −0.104 | 0.100 | 18 | −0.143 | 0.029 | p-values are two-sided

Safety Measures

Treatment-emergent adverse events were those that began or worsened following the first dose of study drug in Period 1. Adverse event monitoring was conducted at each study visit and until 30 days following discontinuation of study drug. Other routine safety assessments included vital signs, electrocardiograms, physical examinations, brief neurological examinations and laboratory tests.

On average, patients reported 109 adverse effects (AEs) (62.6% of subjects receiving treatment) over the study period compared to with 126 AEs (56.0% of subjects) for placebo. Of the individual AEs, 21 subjects reported nausea (12.1% of subjects) compared with 5 subjects (2.2% of subjects) in the placebo group. An overview of the number of subjects with any treatment emergent adverse events (AEs) and those AEs reported by greater than 2 subjects receiving any dose of ABT-894 compared to placebo and atomoxetine is presented in Table 6.

in the primary efficacy endpoint, and validated the use of such measures in adults with ADHD. Treatment with ABT-894 2 mg QD and 4 mg BID doses improved measures of quality of life relative to placebo. ABT-894 administered at 2 mg QD improved measures of sustained attention, inhibitory control, and executive function. ABT-894 administered at 4 mg BID improved quality of life relative to placebo and significantly improved absenteeism. Moreover, ABT-894 generally was safe and well tolerated.

Steady state pharmacokinetic parameters of ABT-894 were determined in randomized, double-blind, placebo-controlled, parallel-design or crossover-design studies conducted with ABT-894. In these studies ABT-894 or matching placebo was administered orally either once daily (QD) or twice daily (BID) to subjects and serial blood samples were collected in order to determine ABT-894 plasma concentrations and pharmacokinetic parameters.

TABLE 6

Adverse Events in >2 Subjects Receiving Active Treatment (Number of (%) of Subjects)

| | Total | | ABT-894 | | | | Atomoxetine |
|---|---|---|---|---|---|---|---|
| | Placebo N = 225 | ABT-894 N = 174 | 1 mg QD N = 46 | 2 mg QD N = 42 | 4 mg QD N = 40 | 4 mg BID N = 46 | 40 mg BID N = 50 |
| | | | Number of subjects with treatment-emergent adverse events | | | | |
| Any Adverse Event | 126 (56.0) | 109 (62.6) | 32 (69.6) | 26 (61.9) | 26 (65.0) | 25 (54.3) | 41 (82.0) |
| Diarrhea | 5 (2.2) | 6 (3.4) | 0 (0) | 2 (4.8) | 3 (7.5) | 1 (2.2) | 1 (2.0) |
| Dry mouth | 8 (3.6) | 3 (1.7) | 2 (4.3) | 0 (0) | 0 (0) | 1 (2.2) | 3 (6.0) |
| Nausea | 5 (2.2) | 21 (12.1) | 2 (4.3) | 6 (14.3) | 9 (22.5) | 4 (8.7) | 10 (20.0) |
| Vomiting | 1 (0.4) | 6 (3.4) | 0 (0) | 1 (2.4) | 4 (10.0) | 1 (2.2) | 1 (2.0) |
| Fatigue | 11 (4.9) | 9 (5.2) | 2 (4.3) | 1 (2.4) | 2 (5.0) | 4 (8.7) | 6 (12.0) |
| Feeling hot and cold | 0 (0) | 0 (0) | 0 (0) | 0 (0) | 0 (0) | 0 (0) | 3 (6.0) |
| Feeling jittery | 4 (1.8) | 0 (0) | 0 (0) | 0 (0) | 0 (0) | 0 (0) | 3 (6.0) |
| Influenza-like illness | 0 (0) | 0 (0) | 0 (0) | 0 (0) | 0 (0) | 0 (0) | 3 (6.0) |
| Upper RTI | 6 (2.7) | 7 (4.0) | 1 (2.2) | 3 (7.1) | 3 (7.5) | 0 (0) | 2 (4.0) |
| Muscle Strain | 1 (0.4) | 3 (1.7) | 3 (6.5) | 0 (0) | 0 (0) | 0 (0) | 0 (0) |
| Decreased appetite | 5 (2.2) | 2 (1.1) | 0 (0) | 0 (0) | 2 (5.0) | 0 (0) | 6 (12.0) |
| Dizziness | 6 (2.7) | 11 (6.3) | 2 (4.3) | 4 (9.5) | 4 (10.0) | 1 (2.2) | 4 (8.0) |
| Headache | 23 (10.2) | 18 (10.3) | 4 (8.7) | 5 (11.9) | 5 (12.5) | 4 (8.7) | 7 (14.0) |
| Lethargy | 1 (0.4) | 1 (0.6) | 0 (0) | 0 (0) | 1 (2.5) | 0 (0) | 3 (6.0) |
| Somnolence | 7 (3.1) | 8 (4.6) | 6 (13.0) | 0 (0) | 0 (0) | 2 (4.3) | 4 (8.0) |
| Parathesia | 1 (0.4) | 0 (0) | 0 (0) | 0 (0) | 0 (0) | 0 (0) | 5 (10.0) |
| Sleep disturbances* | 17 (7.6) | 13 (7.5) | 2 (4.3) | 6 (14.3) | 3 (7.5) | 2 (4.3) | 8 (16.0) |
| Nasal congestion | 0 (0) | 3 (1.7) | 0 (0) | 0 (0) | 0 (0) | 3 (6.5) | 2 (4.0) |

*Sleep disturbances consists of abnormal dreams, initial insomnia, insomnia, middle insomnia, nightmare, sleep disorders A summary of weight and vital signs assessed after four weeks of treatment is presented in Table 7.

TABLE 7

Mean difference from placebo in weight and vital sign for each dose of ABT-894 at final evaluation (last observation carried forward)

| | | Dose of ABT-894 | | | | Atomoxetine |
|---|---|---|---|---|---|---|
| | | 1 mg QD | 2 mg QD | 4 mg QD | 4 mg BID | 40 mg BID |
| Weight (kg) | | 0.48 | 0.09 | 0.04 | −0.08 | −0.73 |
| Vital Signs | Pulse (bpm) | −0.24 | 0.42 | 3.14 | 0.98 | 4.74 |
| | Systolic BP (mm Hg) | 1.36 | 1.07 | −0.08 | −0.48 | 1.16 |
| | Diastolic BP (mm Hg) | 0.28 | 0.62 | 0.23 | −2.21 | 0.72 |

As shown by the data, adults with ADHD showed statistically significantly greater improvement in CAARS:Inv Total score with ABT-894 treatment at 4 mg BID when compared to placebo. Improvement in measures of work productivity (WPAI) and quality of life (AAQoL) correlated with changes After multiple doses of ABT-894, at steady state, for the 2 mg QD dose the $C_{max}$ was about 5 ng/mL, $C_{ave}$ was about 2 ng/mL, $AUC_{24}$ was about 46 ng.h/mL, and $C_{min}$ was about 0.3 ng/mL. After multiple doses of ABT-894, at steady state, for the 4 mg BID dose, the $C_{max}$ was about 11-15 ng/mL, $C_{ave}$ was about 6-10 ng/mL, $AUC_{12}$ was about 72-114 ng.h/mL, and $C_{min}$ was about 2-4 ng/mL.

$T_{max}$ for ABT-894 generally was reached within about 2-4 hours, and particularly within 2-3 hours.

As used herein, $C_{max}$ refers to peak plasma concentration of a therapeutic agent, in this case ABT-894, under steady state conditions.

As used herein, $C_{ave}$ refers to average plasma concentration of a therapeutic agent. in this case ABT-894, under steady state conditions.

As used herein, $C_{min}$ refers to the minimum plasma concentration of a therapeutic agent, in this case ABT-894, under steady state conditions.

As used herein. $T_{max}$ refers to the time required to reach peak concentration.

As used herein, $AUC_{12}$ refers to the area under the curve determined for 12 hours.

As used herein. $AUC_{24}$ refers to the area under the curve determined for 24 hours.

Patient intervention can be for any suitable period of treatment. Although ADHD symptoms may lessen or resolve over time, ADHD is often a chronic, stable condition. Patients with ADHD typically receive chronic, maintenance pharmacologic treatment.

An average adult human patient participating in the subject is about 70 kg in body weight.

CANTAB® neuropsychological tests are commercially available assessment tools for pharmaceutical testing in clinical trials and can be obtained from Cambridge Cognition Ltd.

Atomoxetine is a commercially available non-stimulant drug approved for the treatment of attention-deficit/hyperactivity disorder. The chemical name for atomoxetine is (3R)-N-methyl-3-(2-methylphenoxy)-3-phenyl-propan-1-amine; (R)-N-methyl-3-phenyl-3-(o-tolyloxy)propan-1-amine.

More information regarding atomoxetine can be obtained from the manufacturer, Eli Lilly and Company, under the brand name STRATTERA. The starting atomoxetine dosage for adults, as well as children or teens weighing more than 154 pounds, is 40 mg once daily or 20 mg twice daily. Children and teenagers weighing less than 154 pounds typically start with 0.25 mg of atomoxetine per pound of weight, rounded to the nearest available strength. Among the factors that can affect atomoxetine dosing are age, other medical conditions of the patient, and other medications the patient may be taking.

All patent documents identified in the foregoing description are hereby incorporated by reference in their entirety.

The above Examples are for illustrative purposes only and are not intended to limit the scope of the invention.

What is claimed is:

1. A method of treating attention-deficit/hyperactivity disorder in a subject in need thereof, comprising administering to a human patient in need of treatment for attention-deficit/hyperactivity disorder an amount of 3-(5,6-dichloro-pyridin-3-yl)-1S,5S-3,6-diazabicyclo[3.2.0]heptane or salt thereof that is 4 milligrams administered twice in a twenty-four hour period and the amount of 3-(5,6-dichloro-pyridin-3-yl)-1S,5S-3,6-diazabicyclo[3.2.0]heptane or salt thereof administered provides a plasma area under the curve (AUC) ratio that reduces symptom severity while minimizing adverse drug effect.

2. The method of claim 1, wherein the administration of 3-(5,6-dichloro-pyridin-3-yl)-1S,5S-3,6-diazabicyclo[3.2.0]heptane or salt thereof provides a mean Cmax that is from about 5-15 ng/mL.

3. The method of claim 1, wherein the administration of 3-(5,6-dichloro-pyridin-3-yl)-1S,5S-3,6-diazabicyclo[3.2.0]heptane or salt thereof provides an $AUC_{12}$ for 4 mg BID ranged that is from about 72-114 ng.hr/mL.

* * * * *